US 9,943,255 B2

United States Patent
Pandian et al.

(10) Patent No.: US 9,943,255 B2
(45) Date of Patent: Apr. 17, 2018

(54) METHOD AND A SYSTEM FOR MONITORING OXYGEN LEVEL OF AN ENVIRONMENT

(71) Applicant: Wipro Limited, Bangalore (IN)

(72) Inventors: Panneer Selvam Jayaveera Pandian, Chennai (IN); Vinod Pathangay, Bangalore (IN)

(73) Assignee: WIPRO LIMITED, Bangalore (IN)

( * ) Notice: Subject to any disclaimer, the term of this patent is extended or adjusted under 35 U.S.C. 154(b) by 22 days.

(21) Appl. No.: 14/870,821

(22) Filed: Sep. 30, 2015

(65) Prior Publication Data

US 2017/0027487 A1 Feb. 2, 2017

(30) Foreign Application Priority Data

Jul. 29, 2015 (IN) .............................. 3895/CHE/2015

(51) Int. Cl.
 *A61B 5/00* (2006.01)
 *A61B 5/1455* (2006.01)
 *G01N 33/00* (2006.01)

(52) U.S. Cl.
 CPC ........ *A61B 5/14551* (2013.01); *A61B 5/7271* (2013.01); *A61B 5/742* (2013.01); *G01N 33/0036* (2013.01); *A61B 2560/0242* (2013.01)

(58) Field of Classification Search
 None
 See application file for complete search history.

(56) References Cited

U.S. PATENT DOCUMENTS

| 6,258,201 | B1 | 7/2001 | Krech | |
|---|---|---|---|---|
| 2004/0230108 | A1* | 11/2004 | Melker | A61B 5/0873 600/340 |
| 2007/0032733 | A1* | 2/2007 | Burton | A61B 5/02405 600/509 |
| 2007/0299323 | A1 | 12/2007 | Arns et al. | |

(Continued)

OTHER PUBLICATIONS

Poh, M.Z., McDuff, D.J., Picard, R. W., "Non-contact, automated cardiac pulse measurements using video imaging and blind source separation", Optics Express, vol. 18, No. 10, pp. 1-14, May 2010.*

(Continued)

*Primary Examiner* — Tse Chen
*Assistant Examiner* — Joanne Hoffman
(74) *Attorney, Agent, or Firm* — Finnegan, Henderson, Farabow, Garrett & Dunner LLP

(57) ABSTRACT

The present disclosure relates to a method for monitoring oxygen level of an environment. The method comprises receiving at least one image of the environment comprising plurality of users from a capturing device. Then, at least one region of interest of each of the plurality of users is detected in the at least one image. A video plethysmographic waveform is generated by analyzing the at least one region of interest. Further, Peripheral Capillary Oxygen Saturation ($SPO_2$) based on the video plethysmographic waveform is determined. Thereafter, oxygen level of the environment is determined by averaging the $SPO_2$ level of each of the plurality of users. The determined oxygen level of the environment is compared with predefined oxygen level of the environment and an appropriate action is performed based on the comparison.

16 Claims, 6 Drawing Sheets

(56) References Cited

U.S. PATENT DOCUMENTS

| | | |
|---|---|---|
| 2008/0221401 A1 | 9/2008 | Derchak et al. |
| 2011/0183305 A1 | 7/2011 | Orbach |
| 2014/0121540 A1 | 5/2014 | Raskin |
| 2016/0220128 A1* | 8/2016 | Den Brinker ........ A61B 5/7203 |

OTHER PUBLICATIONS

Bal, U. "Non-contact estimation of heart rate and oxygen saturation using ambient light", Biomedical Optics Express, vol. 6, No. 1, 2014.*

Chapter 8, Cluster analysis: basic COncepts and Algorithms, pp. 488-568, 2005.*

Gong, E. and Bouhenguel, J. "Vitals are Vital! Visual Vital Metric Detection for Multiple Subjects", Stanford, 2014, herein referred to as "Gong".*

Kumar, M., Veeraraghavan, A. and Sabharval, A., "DistancePPG: Robust non-contact vital signs monitoring using a camera", Optical Society of America, Mar. 2015, herein referred to as "Kumar".*

Bates, Jason H. T. et al.; "Unrestrained video-assisted plethysmography: a noninvasive method for assessment of lung mechanical function in small animals"; Innovated Methodology; Journal of Applied Physiology, vol. 104, pp. 253-261, 2008.

* cited by examiner

METHOD AND A SYSTEM FOR MONITORING OXYGEN LEVEL OF AN ENVIRONMENT

PRIORITY CLAIM

This U.S. patent application claims priority under 35 U.S.C. § 119 to India Application No. 3895/CHE/2015, filed Jul. 29, 2015. The entire contents of the aforementioned application are incorporated herein by reference.

FIELD OF THE DISCLOSURE

The present subject matter relates to a non-invasive monitoring system, and more particularly, but not exclusively to system and method for monitoring oxygen level of an environment.

BACKGROUND

Oxygen concentration in the atmosphere needs to be around 20% of the total air volume for humans to breathe effectively. If the oxygen level decreases, humans face problems such as increase in heart rate, increase in respiration rate, fatigue, emotional upset, nausea, vomiting, etc.

It is observed that the oxygen level drops severely under various scenarios, such as, high altitude, underground places, places with concentrated gathering of people, etc. For activities like mineral excavation, miners need to go inside the mines which are deep underground pocket mostly having very low oxygen level. An example of a place having high concentration of people may be a theater or a movie hall.

Currently, there exist several approaches to detect the oxygen level in a place. However, the existing mechanisms are based on sensors which directly measure the oxygen level in a particular area or place. These sensors need to be spread across a place and placed at appropriate positions so as to get a right value. In many scenarios, like in the case of a mine, numerous such sensors need to be used to and are at times difficult to cover the whole area.

Alternatively, there exist few other mechanisms of detecting worker or person health condition which are indicative of oxygen level in that surrounding. However most of these mechanisms are intrusive in nature. Systems collect physiological parameters of the worker through wired or wireless means and then derive the condition of the person/worker based on such data.

SUMMARY

One or more shortcomings of the prior art are overcome and additional advantages are provided through the present disclosure. Additional features and advantages are realized through the techniques of the present disclosure. Other embodiments and aspects of the disclosure are described in detail herein and are considered a part of the claimed disclosure.

In one embodiment, the present disclosure relates to a method for monitoring oxygen level of an environment. The method comprises receiving at least one image of the environment comprising plurality of users from a capturing device, detecting at least one region of interest of each of the plurality of users in the at least one image, generating a video plethysmographic waveform by analyzing the at least one region of interest, determining peripheral capillary oxygen saturation ($SPO_2$) level of each of the plurality of users based on the video plethysmographic waveform. An average $SPO_2$ of each of the users of plurality of users corresponds to a value denoting oxygen level of the environment. The method comprises comparing the determined oxygen level with a predefined oxygen level for the environment and performing one or more actions based on the comparison for monitoring oxygen level of the environment.

In another embodiment, the present disclosure relates to a monitoring device for monitoring oxygen level of an environment. The device further comprises a processor and a memory communicatively coupled to the processor, where the memory stores processor-executable instructions, which, on execution, cause the processor to perform operations comprising receiving at least one image of the environment comprising plurality of users from a capturing device, detecting at least one region of interest of each of the plurality of users in the at least one image, generating a video plethysmographic waveform by analyzing the at least one region of interest determining peripheral capillary oxygen saturation ($SPO_2$) level of each of the plurality of users based on the video plethysmographic waveform. An average $SPO_2$ of each of the users of plurality of users corresponds to a value denoting oxygen level of the environment. The operation comprises comparing the determined oxygen level with a predefined oxygen level for the environment and performing one or more actions based on the comparison for monitoring oxygen level of the environment.

In another embodiment, the present disclosure relates to a non-transitory computer readable medium including instructions stored thereon that when processed by at least one processor causes a monitoring device to perform the act of receiving al least one image of an environment comprising plurality of users from capturing device, detecting at least one region of interest of each of the plurality of users in the at least one image, generating a video plethysmographic waveform by analyzing the at least one region of interest, determining peripheral capillary oxygen saturation ($SPO_2$) level of each of the plurality of users based on the video plethysmographic waveform. An average $SPO_2$ of each of the users of plurality of users corresponds to a value denoting oxygen level of the environment. The operation comprises comparing the determined oxygen level with a predefined oxygen level for the environment and performing one or more actions based on the comparison for monitoring oxygen level of the environment.

The foregoing summary is illustrative only and is not intended to be in anyway limiting. In addition to the illustrative aspects, embodiments, and features described above, further aspects, embodiments, and features will become apparent by reference to the drawings and the following detailed description.

BRIEF DESCRIPTION OF THE DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

Figure 1:
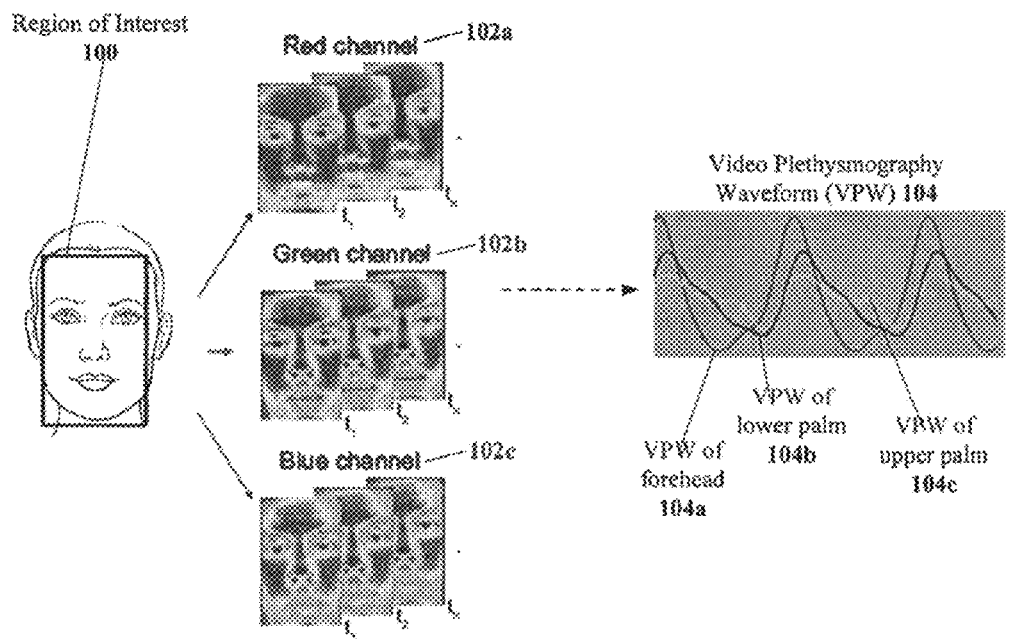
FIG. 1 illustrates an exemplary embodiment of generation of Video Plethysmography Waveforms (VPW) of Region of Interest (ROI) of a user to monitor oxygen level of an environment in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

The present disclosure relates to a method and a monitoring device for monitoring oxygen level of an environment. The method comprises receiving at least one image of an environment comprising plurality of users from a video captured by a capturing device which is communicatively connected to the monitoring device. In an embodiment, the at least one image is a series of images taken from a video frame. In an embodiment, the capturing device is configured in the monitoring device and/or coupled to the monitoring device. In an embodiment, the capturing device can be connected to the monitoring device over a network comprising wired or wireless network. From the received image, at least one image of the environment comprising plurality of users, regions of interest of each of the plurality of user is detected. The regions of interest may be the uncovered body parts of the plurality of users. Then, Video Plethysmographic Waveforms (VPW) are generated by analyzing the regions of the interest. Particularly, the video plethysmographic waveforms are generated based on pixel variations of the at least one image of the user corresponding to the detected regions of the interest. Using the VPW, Peripheral capillary Oxygen Saturation ($SPO_2$) of each of the plurality of users is determined. Then, an average $SPO_2$ of each of the plurality of users is determined. This average $SPO_2$ value is then used to determine a corresponding oxygen level of the environment. The determined oxygen level of the environment is monitored by the monitoring device by comparing it with a predefined oxygen level for the environment. An action is performed accordingly based on the comparison.

FIG. 1 shows VPW 104 generated from the region of interest 100 of a user. Consider the regions of interest 100 are face, upper palm of the user and lower palm of the user. The VPW 104 is generated from three different channels comprising Red channel 102a, Green Channel 102b and Blue Channel 102c, which are formed from the regions of interest 100 of the at least one image in the illustrated FIG. 1, VPW 104 is generated for each regions of the interest based on the corresponding channel. That is, VPW 104 is generated for the face, the upper palm and the lower palm region of the user. Based on the video plethysmographic waveforms, at least one of, but not limiting to, Peripheral capillary Oxygen Saturation ($SPO_2$), respiratory rate and heart rate of the user is determined. In an example embodiment, the present invention determines the $SPO_2$ of each of the plurality of users. A first average of $SPO_2$ is obtained by averaging the determined $SPO_2$ of each of the plurality of users. An average of first average of $SPO_2$ corresponds to an oxygen level of the environment.

In an embodiment, the image of the environment is divided into plurality of clusters such that each cluster of the plurality of clusters comprises a predefined number of users of the plurality of users. The $SPO_2$ of predefined number of users of the corresponding cluster is determined using VPW. The first avenge of $SPO_2$ of predefined number of users may correspond to oxygen level of the corresponding cluster. Further, the average of oxygen level of each of the plurality of clusters may determine the oxygen level of the environment.

Figure 2:
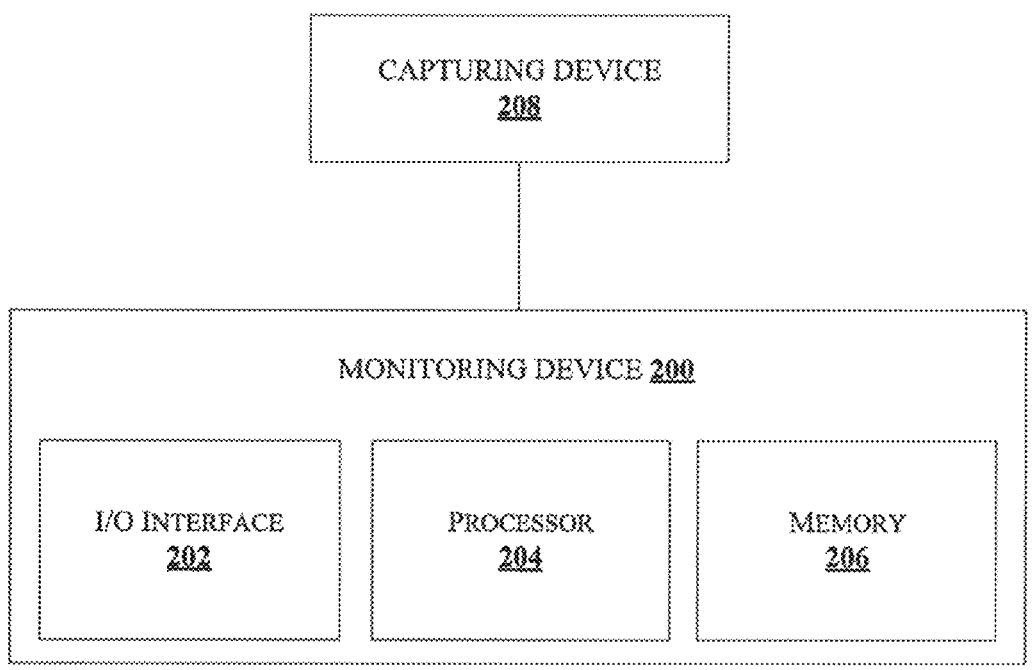
FIG. 2 illustrates an exemplary embodiment of a monitoring device for monitoring oxygen level of an environment using Video Plethysmographic Waveforms (VPW) in accordance with some embodiments of the present disclosure.

FIG. 2 illustrates an exemplary block diagram of a monitoring device 200 for monitoring oxygen level of an environment using Video Plethysmographic Waveforms (VPW) in accordance with some embodiments of the present disclosure. In one implementation, the monitoring device 200 may be implemented in a variety of computing systems, such as a laptop computer, a desktop computer, a Personal Computer (PC), a notebook, a smartphone, a tablet, e-book readers (e.g., Kindles and Nooks), a server, a network server, and the like. In one example, the monitoring device 200 is configured to monitor oxygen level of an environment non-invasively. Particularly, the oxygen level of the environment comprising plurality of users is detectable from video frames captured. Thus, any wearable device and/or contact of the plurality users with the monitoring device 200 and/or any device connected to the monitoring device 200 are excluded. The components of the monitoring device 200 are explained in detail below sections of the description.

In an embodiment, the monitoring device 200 is communicatively connected to at least one capturing device 208. In another embodiment, the capturing device 208 may be configured within the monitoring device. In one example, the capturing device 208 may include, but is not limited to, a camera 208, a video camera, digital camera, Charged Couple Device (CCD) camera, an image camera. Universal Serial Bus (USB) camera, video cards with composite or S-video devices and other such camera which is capable of capturing video frames of users. Here, each of the plurality of users is a person or any living being whose at least one image is captured and $SPO_2$ is to be determined. In one implementation, the at least one capturing device 208 is a separate device which is coupled to the monitoring device 200 and/or connected to the monitoring device 200 over a network (not shown). In one implementation, the at least one capturing device 208 is configured in one or more user devices (not shown) used by the plurality of users. The one or more user devices include, but are not limited to, computing systems, such as a laptop computer, a desktop computer, a Personal Computer (PC), a notebook, a smartphone, a smart watch, a wearable device, a tablet, e-book readers (e.g., Kindles and Nooks). In such a case, the monitoring device 200 may be communicatively connected to the one or more user devices and one or more servers (not shown). In one implementation, the at least one image of the environment can be received from the one or more user devices and/or the one or more servers (not shown) by the monitoring device 200. In such a case, the at least one image of the environment may be stored in files/library of the one or more user devices, and/or memory chip, USBs, hard disks, and/or the one or more servers. Here, the one or more servers are the servers associated with the monitoring device 200 and/or third party servers accessible by the monitoring device 200. In one implementation, the at least one image of the environment can be downloaded from Internet.

In the illustrated FIG. 2, monitoring device 200 comprises an I/O interface 202, a central processing unit ("CPU" or "processor") 204 having one or more processing units, and a memory 206 in accordance with some embodiments of the present disclosure.

The I/O interface 202 is a medium through which the at least one image of the environment can be received from the at least one capturing device 208, and/or the one or more user devices and/or the one or more servers. Further, the I/O interface 202 is configured to receive a feedback from the plurality of users and/or operators who are capable of operating the monitoring device 200. The I/O interface 202 provides results of monitoring the oxygen level of the environment. Particularly, the oxygen level of the environment is provided to a display unit (not shown in FIG. 1), and the one or more user devices. The I/O interlace 202 is coupled with the processor 204.

The processor 204 may comprise at least one data processor for executing program components for processing system-generated video plethysmographic waveforms of corresponding regions of interest of the user from the at least one image of the environment. The processor 204 is configured to detect at least one region of interest of each of the plurality of users. In an exemplary embodiment, the region of interest of the user is uncovered body part of the user. The processor 202 analyzes the at least one region of interest of the user and forms colored histogram i.e. red channel, and/or green channel and/or blue channel of the at least region of interest. In an embodiment, only green channel of the at least one region of interest is analyzed. Then, the processor 202 generates Video Plethysmographic Waveforms (VPW) for the colored histogram of the at least one region of interest of the user. The processor 202 generates the VPW based on pixel variations of the at least one image of the region of interest of each of the plurality of users. The processor 202 determines $SPO_2$ of the user based on the VPW. The processor 202 determines a first average by averaging the $SPO_2$ of each of the plurality of users. Further, the processor 202 determines an average $SPO_2$ by averaging each of the first averages, which corresponds to oxygen level of the environment. The processor 202 compares the determined oxygen level of the environment with a predefined oxygen level for the environment. The processor 202 is configured to perform one or more actions based on the comparison.

In an embodiment, the processor 202 is configured to perform one of, monitoring the oxygen level, storing the oxygen level for further analysis, providing a notification and providing supply of oxygen to the environment. In one implementation, the monitoring device 200 alerts the plurality of users if the environmental oxygen level does not match the predefined oxygen level.

The memory 206 stores instructions which are executable by the at least one processor 204. In an embodiment, the memory 206 stores image information, region of interest data, VPW data, $SPO_2$ data, environmental oxygen level data and predefined oxygen level data. In an embodiment, the image information, the region of interest data, the VPW data, the $SPO_2$ data, and the predefined oxygen level data are stored as one or more data required for determining the oxygen level of the environment as described in the following description of the disclosure.

Figure 3:
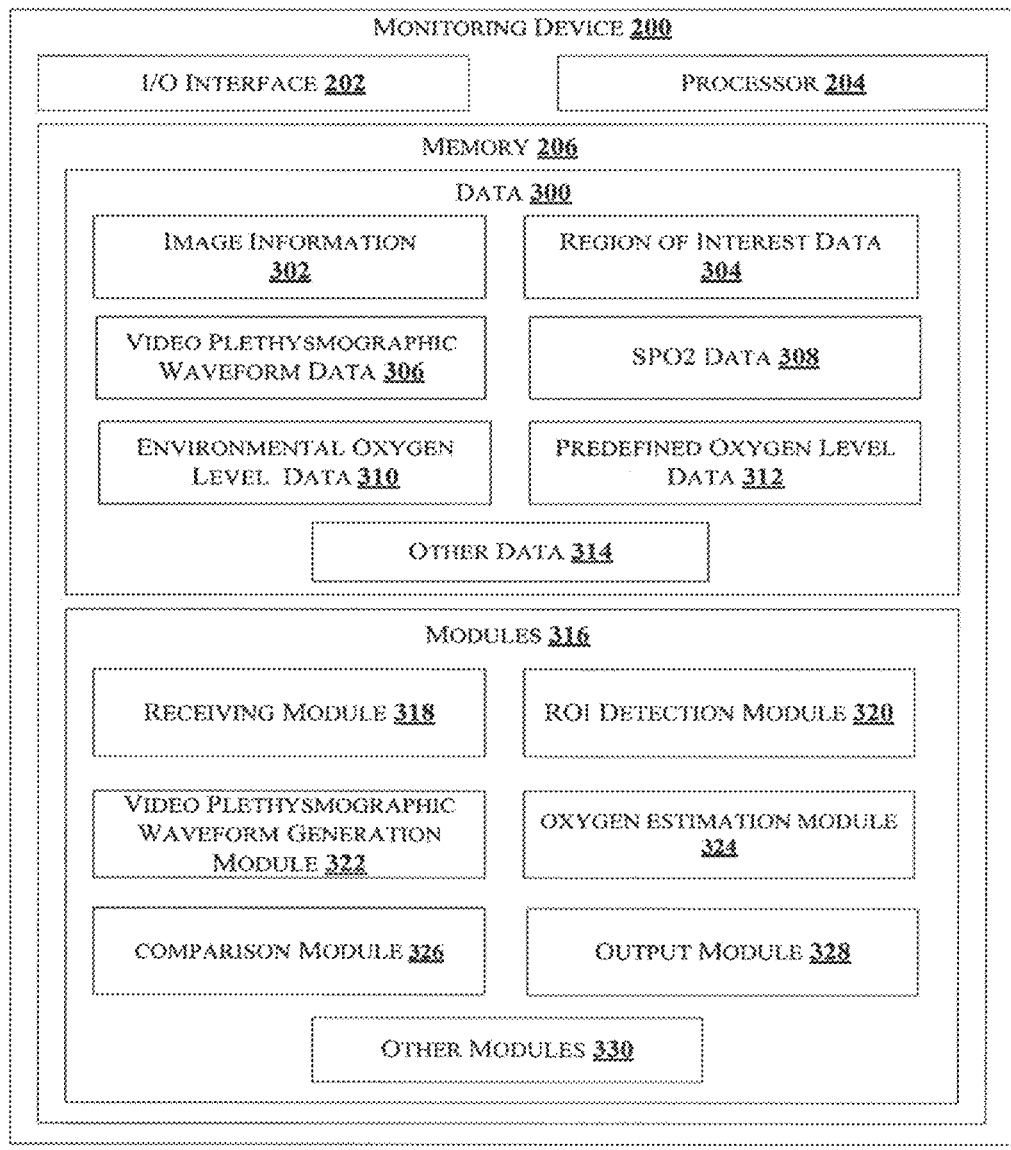
FIG. 3 illustrates a detailed block diagram of an exemplary monitoring device with various data and modules for monitoring oxygen level of an environment in accordance with some embodiments of the present disclosure.

FIG. 3 illustrates a block diagram of the exemplary monitoring device 200 with various data and modules for determining the oxygen level of an environment in accordance with some embodiments of the present disclosure. In the illustrated FIG. 3, the one or more data 300 and the one or more modules 316 stored in the memory 206 are described herein in detail.

In an embodiment, the one or more data 300 may include, for example, the image information 302, the region of interest data 304, the VPW data 306, the $SPO_2$ data 308, the environmental oxygen data 310 and predefined oxygen level data 312, and other data 314 for monitoring the oxygen level of the environment. In an embodiment, the data 300 including the image information 302, the region of interest data 304, the VPW data 306 and the $SPO_2$ data 308 are the data which are detected and/or calculated in real-time. Particularly, the image information 302, the region of interest data 304, the VPW data 306 and the $SPO_2$ data 308 are not predefined or preconfigured beforehand in the monitoring device 200. The predefined oxygen level data 312 is defined beforehand and stored in the monitoring device 200.

The image information 302 refers to information of pixels of the at least one image of the user. The information of the pixels of the at least image may include, but is not limiting to, pixel size, pixel color and number of pixels of the at lent one image.

The region of interest data 304 refers to the at least one region of interest of the user in the at least one image. In an embodiment, the uncovered parts of body of the user may be referred to as region of interest. For example, face and hands may be the at least one region of interest of the user.

The VPW data 306 refers to the VPW of the corresponding at least one region of interest, which is being generated based on pixel variations of the at least one image of the user. The VPW data 306 includes details of the VPW including depth, width, altitude, distortion/noise of the waveforms being generated. The $SPO_2$ data 308 refers to at least one physiological characteristic being determined from the VPW.

The other data 314 may refer to such data which can be referred for monitoring the oxygen level of the environment.

In an embodiment, the one or more data 300 in the memory 206 are processed by the one or more modules 316 of the monitoring device 200. The one or more modules 316 may be stored within the memory 206 as shown in FIG. 3. In an example, the one or more modules 316, communicatively coupled to the processor 204, may also be present outside the memory 206 and implemented as hardware. As used herein, the term module refers to an application specific integrated circuit (ASIC), an electronic circuit, a processor (shared, dedicated, or group) and memory that execute one or more software or firmware programs, a combinational logic circuit, and/or other suitable components that provide the described functionality.

In one implementation, the one or more modules 316 may include, for example, a receiving module 318, a Region of Interest (ROI) detection module 320, a Video Plethysmograph Wave (VPW) generation module 322, an oxygen estimation module 324, a comparison module 326 and an output module 328. The memory 206 may also comprise other modules 330 to perform various miscellaneous functionalities of the monitoring device 200. It will be appreciated that such aforementioned modules may be represented as a single module or a combination of different modules.

The receiving module 318 receives the at least one image of the user from the capturing device 208 and/or the one or more user devices and/or the one or more servers. For example, consider the capturing device 208 in places with high altitude, underground places, places with concentrated gathering of people, etc. In such a case, the at least one image of an environment comprising plurality users is captured which is in turn received by the receiving module 318. Also, the receiver module 318 may receive feedback from the plurality of users. Based on the feedback received, an appropriate action is performed.

The ROI detection module 320 detects the at least one region of interest of each of the plurality of users from the received at least one image. In an embodiment, the ROI detection module 320 detects the at least one region of interest which is body part of the user that is not covered. For example, the ROI detection module 320 can detect face, lower palm and upper palm as the region of interest from the at least one image of the user.

The Video Plethysmographic Waveform (VPW) generation module 322 analyzes the at least one region of interest of the user being detected. The VPW generation module 322 generates a color histogram i.e. video plethysmographic gradient histogram of the at least one region of interest. In an embodiment, the color histogram includes, but is not limited to, red channel, green channel and blue channel. Then, the waveforms of the at least one region of interest is generated from the color histogram in a form of corresponding trace, for example, red trace, green trace and blue trace. Then, the VPW generation module 322 generates the VPW of the corresponding trace. In an example, the VPW generation module 322 may generate the VPW by monitoring the at least one regions of interest for a predefined time period. For instance, the VPW generation module 322 may monitor the region of interest and receive video feed of the region of interest for 30 seconds. Thereafter, the VPW generation module 322 may generate the VPW for the 30 seconds to identify the $SPO_2$ of each of the plurality of users.

The oxygen estimation module 324 determines $SPO_2$ of each of the plurality of users based on the VPW being generated. Then, the oxygen estimation module 324 obtains a first average by averaging the $SPO_2$ of each of the plurality of users. An average $SPO_2$ is determined by averaging each of the first average of $SPO_2$, which has a corresponding oxygen level of the environment. The oxygen estimation module 324 calculates the $SPO_2$ by using the following formula:

$$SpO_2\% = \left(\frac{HbO2}{Hb + HbO2}\right) * 100\% \qquad (1)$$

In the above equation, $HbO_2$ refers to hemoglobin of the blood and $Hb+HbO_2$ refers to oxy-hemoglobin. The average of the $SPO_2$ for a cluster is calculated as follows:

$$\text{Average } SpO2 \text{ for } n \text{ image frames} = 1/n \sum_{i=1}^{n}(SpO_2)_1 \qquad (2)$$

In the above formula 'n' denotes the number of images derived from the video captured for n unit of time and 'i' denote the count variable for unit image frame derived from the captured video. In an example embodiment, if the video of the environment is captured for 5 time units, the images are derived for every time unit. Therefore, 5 image frames are derived from the captured video. Equation 2 is applied to calculate the first average of $SPO_2$ for one cluster. Similarly, equation 2 is applied to each of the plurality of clusters to estimate the $SPO_2$ level of the environment.

In an embodiment, for each of the first average of $SPO_2$, corresponding oxygen level is assigned by the oxygen estimation module 324. Thereby, averaging the corresponding oxygen level of each of plurality of clusters provides the oxygen level of the environment.

The comparison module 326 compares the determined environmental oxygen level data 310 with the predefined oxygen level data 312 for the environment. If the environmental oxygen level data 310 matches with the predefined oxygen level data 312, then the monitoring device 200 continues to monitor the environment. If the environmental oxygen level data 310 is less than the predefined oxygen level data 312, then one or more actions are performed by an output module 328.

The output module 328 provides the environmental oxygen level data 310 to at least one of the audio unit, display unit, the one or more user devices and the one or more servers. In an embodiment, the feedback is received from the user by the receiving module 318 and the predefined oxygen level is updated by the processor 204 based on the feedback. Also, the output module 328 performs one of, monitoring the oxygen level, storing the oxygen level for further analysis, providing a notification to a display unit and providing supply of oxygen to the environment.

Figure 4:
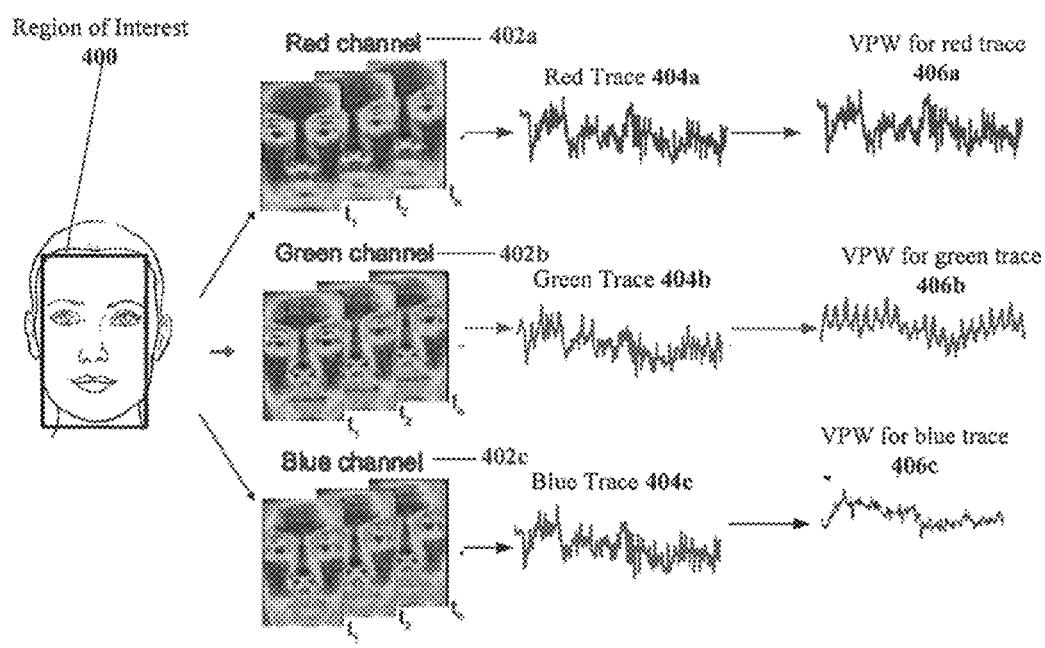
FIG. 4 shows the Video Plethysmographic Waveforms (VPW) being generated for the at least one region of interest in accordance with some embodiments of the present disclosure.

FIG. 4 shows the VPW being generated for the at least one region of interest 400. For example, the image of the user is captured for 'n' number of times i.e. 'n' number of frames of second i.e. t1, t2, . . . , tn of the image of the user is received. Consider, the region of interest 400 is face. Then, the color histogram of the face is generated with red channel 402a, with green channel 402b and blue channel 402c for each of the frames. Then, for each color histogram, the waveforms in the form of the traces having red trace 404a, green trace 404b and blue trace 404c is formed. Then, for each trace, VPW 406a, 406b and 406c is generated as shown in FIG. 4. In an embodiment, the VPW is generated based on the pixel variations of the at least one image, corresponding to each of the at least one region of interest.

Figure 5:
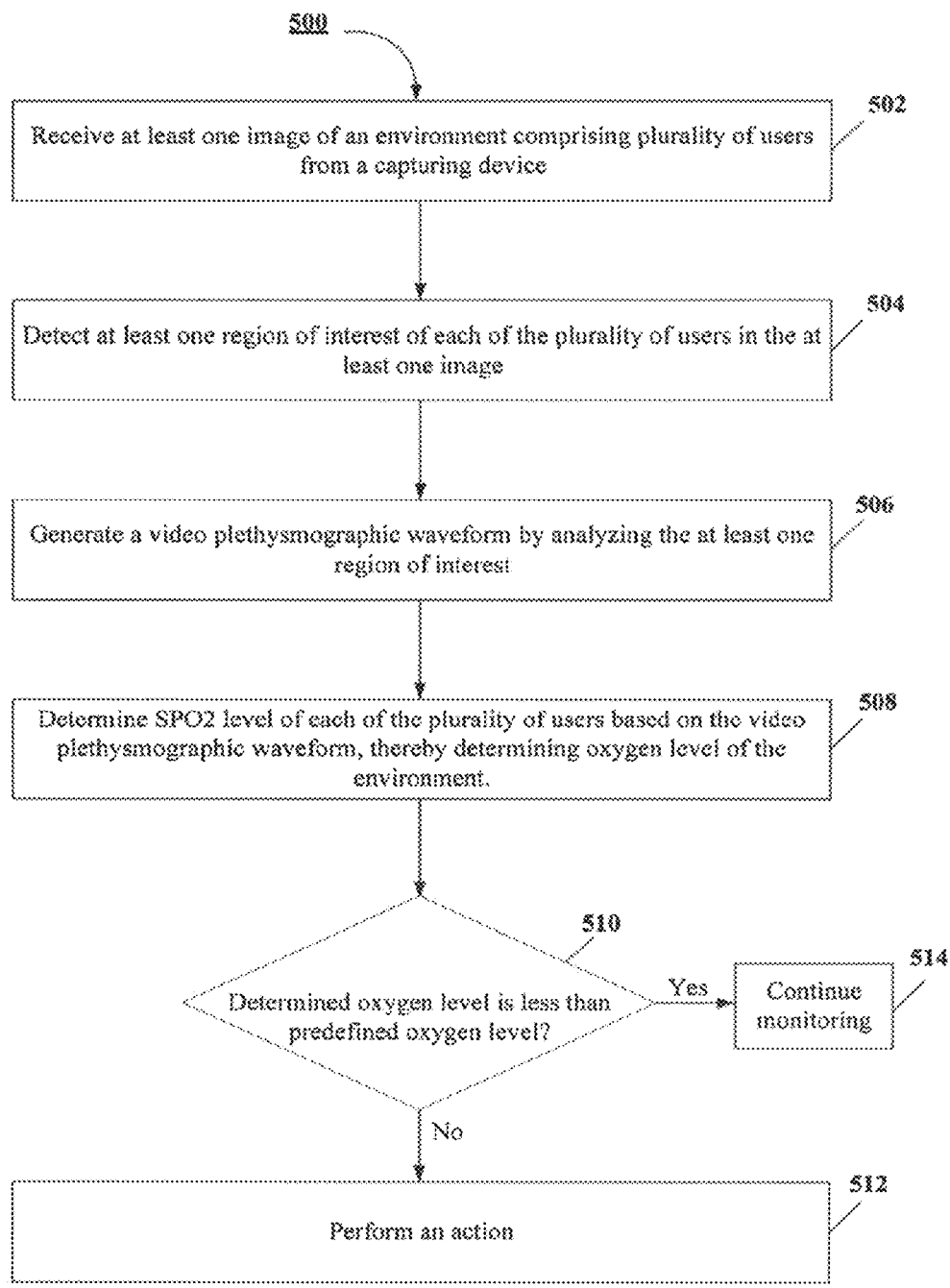
FIG. 5 shows a flowchart illustrating a method for monitoring oxygen level of an environment in accordance with some embodiments of the present disclosure.

FIG. 5 shows a flowchart illustrating a method 500 for monitoring oxygen level of an environment in accordance with some embodiments of the present disclosure.

As illustrated in FIG. 5, the method comprises one or more blocks for monitoring oxygen level of an environment. The method 500 may be described in the general context of computer executable instructions. Generally, computer executable instructions can include routines, programs, objects, components, data structures, procedures, modules, and functions, which perform particular functions or implement particular abstract data types.

The order in which the method 500 is described is not intended to be construed as a limitation, and any number of the described method blocks can be combined in any order to implement the method. Additionally, individual blocks may be deleted from the methods without departing from the scope of the subject matter described herein. Furthermore, the method can be implemented in any suitable hardware, software, firmware, or combination thereof.

At block 502, the at least one image of an environment comprising plurality of users is received from a receiving module 318, and/or the one or more user devices and/or the one or more servers.

At block 504, the at least one region of interest of each of the plurality of users is detected by the ROI detection module 320. In an embodiment, uncovered body part of the user is detected as the at least one region of interest.

At block 506, the VPW of the corresponding at least one region of interest is generated by analyzing the corresponding at least one region of interest by the VPW generation module 322. In an embodiment, the video plethysmographic waveform is generated based on pixel variations of the image, corresponding to each of the at least one region of interest.

At block 508, $SPO_2$ of each of the plurality of users is determined by the oxygen estimation module 324 based on the VPW. The method further comprises determining a first average by averaging $SPO_2$ of each of the plurality of users. The method further comprises averaging each of the first average to determine the average $SPO_2$ of the environment. Lastly, the method comprises assigning corresponding predefined oxygen level to the average $SPO_2$ of the environment.

At block 510, the determined oxygen level of the environment is compared with the predefined oxygen level for the environment by the comparison module 326. If the determined oxygen level does not matches with the predefined oxygen level then process goes to block 512 via "No". If the oxygen level matches with the predefined oxygen level then process goes to block 514 via "Yes".

At block 512, the output module 328 performs one of, monitoring the oxygen level, storing the oxygen level for further analysis, providing a notification to a display unit and providing supply of oxygen to the environment. In an embodiment, a feedback is received from a user by the receiving module 318 and the predefined oxygen level is updated by the output module 328 based on the feedback.

Computer System

Figure 6:
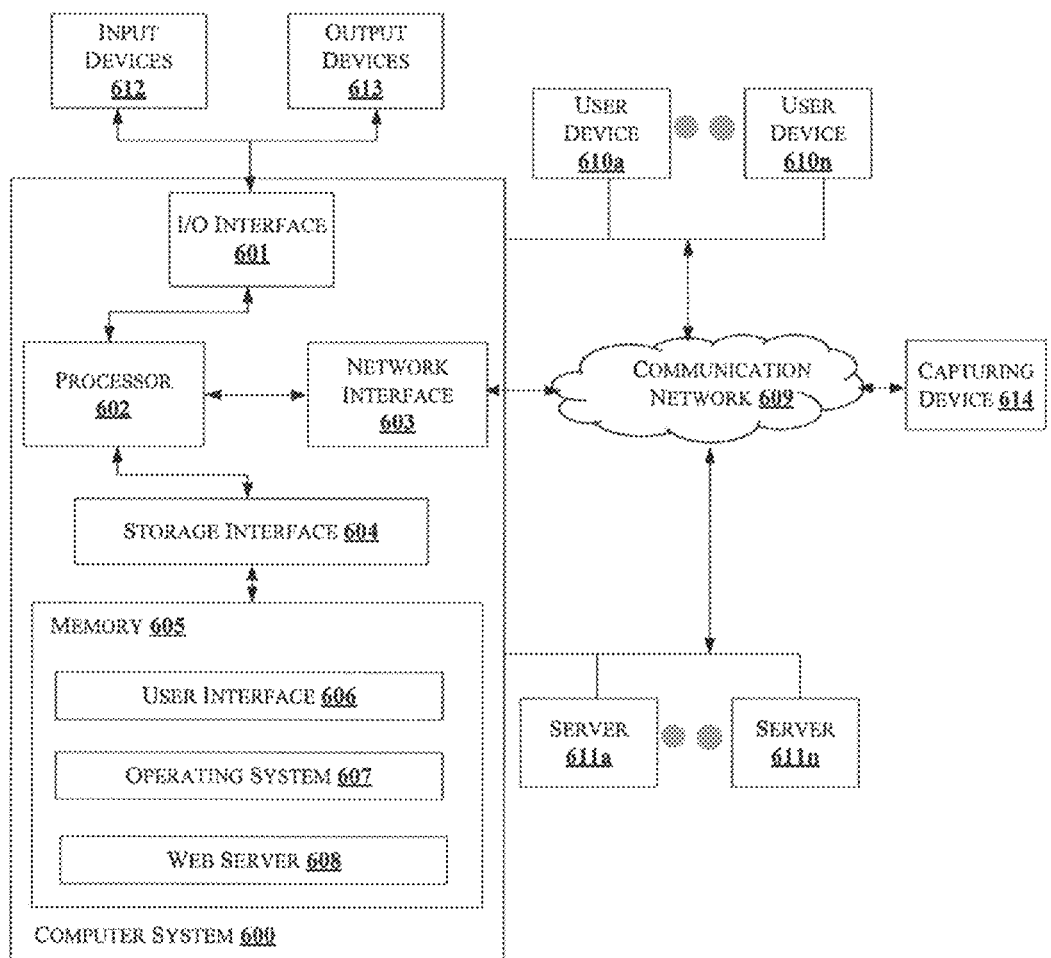
FIG. 6 is a block diagram of an exemplary computer system for implementing embodiments consistent with the present disclosure.

FIG. 6 illustrates a block diagram of an exemplary computer system 600 for implementing embodiments consistent with the present disclosure. In an embodiment, the computer system 600 is used to implement the monitoring device 200. The computer system 600 may comprise a central processing unit ("CPU" or "processor") 602. The processor 602 may comprise at least one data processor for executing program components for executing system-generated video plethysmographic waveform for the corresponding region of interest. The processor 602 may include specialized processing units such as integrated system (bus) controllers, memory management control units, floating point units, graphics processing mats, digital signal processing units, etc.

The processor 602 may be disposed in communication with one or more input output (I/O) devices (not shown) via I/O interface 601. The I/O interface 601 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 601, the computer system 600 may communicate with one or more I/O devices. For example, the input device may be an antenna, keyboard, mouse, joystick, (infrared) remote control, camera, card reader, fax machine, dongle, biometric reader, microphone, touch screen, touchpad, trackball, stylus, scanner, storage device, transceiver, video device/source, etc. The output device may be a printer, fax machine, video display (e.g., cathode ray tube (CRT), liquid crystal display (LCD), light-emitting diode (LED), plasma. Plasma display panel (PDP). Organic light-emitting diode display (OLED) or the like), audio speaker, etc.

In some embodiments, the computer system 600 is connected to the one or more user devices 611a, . . . , 611n, the one or more servers 610a, . . . , 610n and the camera 614 through a communication network 609. The processor 602 may be disposed in communication with the communication network 609 via a network interface 603. The network interface 603 may communicate with the communication network 609. The network interface 603 may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 609 may include, without limitation, a direct interconnection, local area network (LAN), wide area network (WAN), wireless network (e.g., using Wireless Application Protocol), the Internet, etc. Using the network interface 603 and the communication network 609, the computer system 600 may communicate with the one or more user devices 611a, . . . , 611n, the one or more servers 610a, . . . , 610n and the camera 614. The network interface 603 may employ connection protocols include, but not limited to, direct connect, Ethernet (e.g., twisted pair 10/100/1000 Base T), transmission control protocol/internet protocol (TCP/IP), token ring, IEEE 802.11a/b/g/n/x, etc.

The communication network 609 includes, hut is not limited to, a direct interconnection, an e-commerce network, a peer to peer (P2P) network, local area network (LAN), wide area network (WAN), wireless network (e.g., using Wireless Application Protocol), the Internet, Wi-Fi and such. The first network and the second network may either be a dedicated network or a shared network, which represents an association of the different types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the first network and the second network may include a variety of network devices, including routers, bridges, servers, computing devices, storage devices, etc.

In some embodiments, the processor 602 may be disposed in communication with a memory 605 (e.g., RAM, ROM, etc. not shown in FIG. 6) via a storage interface 604. The storage interface 604 may connect to memory 605 including, without limitation, memory drives, removable disc drives, etc., employing connection protocols such as serial advanced technology attachment (SATA). Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 605 may store a collection of program or database components, including, without limitation, user interface 606, an operating system 607, web server 608 etc. In some embodiments, computer system 600 may store user/application data 606, such as the data, variables, records, etc. as described in this disclosure. Such databases may be implemented as fault-tolerant, relational, scalable, secure databases such as Oracle or Sybase.

The operating system 607 may facilitate resource management and operation of the computer system 600. Examples of operating systems include, without limitation, Apple Macintosh OS X, Unix, Unix-like system distributions (e.g., Berkeley Software Distribution (BSD). FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like.

In some embodiments, the computer system 600 may implement a web browser 607 stored program component. The web browser 608 may be a hypertext viewing application, such as Microsoft Internet Explorer, Google Chrome, Mozilla Firefox, Apple Safari, etc. Secure web browsing may be provided using Secure Hypertext Transport Protocol (HTTPS), Secure Sockets Layer (SSL), Transport Layer Security (TLS), etc. Web browsers 608 may utilize facilities such as AJAX, DHTML, Adobe Flash, JavaScript, Java, Application Programming Interfaces (APIs), etc. In some embodiments, the computer system 600 may implement a mail server stored program component. The mail server may be an Internet mail server such as Microsoft Exchange, or the like. The mail server may utilize facilities such as ASP, ActiveX, ANSI C++/C#, Microsoft.NET, CGI scripts, Java, JavaScript, PERL, PHP, Python, WebObjects, etc. The mail server may utilize communication protocols such as Internet Message Access Protocol (IMAP), Messaging Application Programming Interface (MAPI), Microsoft Exchange, Post Office Protocol (POP), Simple Mail Transfer Protocol (SMTP), or the like. In some embodiments, the computer system 600 may implement a mail client stored program component. The mail client may be a mail viewing application, such as Apple Mail, Microsoft Entourage, Microsoft Outlook, Mozilla Thunderbird, etc.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include Random Access Memory (RAM), Read-Only Memory (ROM), volatile memory, nonvolatile memory, hard drives, CD ROMs, DVDs, flash drives, disks, and any other known physical storage media.

Advantages of the Embodiment of the Present Disclosure are Illustrated Herein

Embodiments of the present disclosure are capable of monitoring oxygen level of an environment using just a camera, that is, from image clips or video clips of the environment comprising plurality of users. In such a way, usage of wearable devices is eliminated, user contact is eliminated and also the application of*the present disclosure is cost effective.

Embodiments of the present disclosure reduce measuring physiological characteristics erroneously by generating video plethysmographic waveforms which actually indicates the actual $SPO_2$ of the user.

Embodiments of the present disclosure provide dynamic technique of monitoring the oxygen level of the environment using the images of an environment comprising plurality of users in real-time and the video plethysmographic waveforms corresponding to the region of interest of each of the plurality of users from the image.

Embodiments of the present disclosure can detect oxygen concentration in an environment and can alert the near users using VPW. The present invention reduces the number of sensors to be installed.

Embodiments of the present disclosure can make use of existing cameras to determine oxygen level of the environment. Also, the oxygen level of the environment can be analyzed for the prerecorded videos.

Embodiments of the present disclosure can be used when VPW is correlated with other atmospheric sensors to analyze the impact of other atmospheric gases which causes the oxygen level to fluctuate.

The described operations may be implemented as a method, system or article of manufacture using standard programming and/or engineering techniques to produce software, firmware, hardware, or any combination thereof. The described operations may be implemented as code maintained in a "non-transitory computer readable medium", where a processor may read and execute the code from the computer readable medium. The processor is at least one of a microprocessor and a processor capable of processing and executing the queries. A non-transitory computer readable medium may comprise media such as magnetic storage medium (e.g., hard disk drives, floppy disks, tape, etc.), optical storage (CD-ROMs. DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. Further, non-transitory computer-readable media comprise all computer-readable media except for a transitory. The code implementing the described operations may further be implemented in hardware logic (e.g., an integrated circuit chip, Programmable Gate Array (PGA), Application Specific Integrated Circuit (ASIC), etc.).

Still further, the code implementing the described operations may be implemented in "transmission signals", where transmission signals may propagate through space or through a transmission media, such as an optical fiber, copper wire, etc. The transmission signals in which the code or logic is encoded may further comprise a wireless signal, satellite transmission, radio waves, infrared signals, Bluetooth, etc. The transmission signals in which the code or logic is encoded is capable of being transmitted by a transmitting station and received by a receiving station, where the code or logic encoded in the transmission signal may be decoded and stored in hardware or a non-transitory computer readable medium at the receiving and transmitting stations or devices. An "article of manufacture" comprises non-transitory computer readable medium, hardware logic, and/or transmission signals in which code may be implemented. A device in which the code implementing the described embodiments of operations is encoded may comprise a computer readable medium or hardware logic. Of course, those skilled in the art will recognize that many modifications may be made to this configuration without departing from the scope of the invention, and that the article of manufacture may comprise suitable information bearing medium known in the art.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIG. 5 show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

White various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference Number | Description |
| --- | --- |
| 200 | Monitoring Device |
| 202 | I/O Interface |
| 204 | Processor |
| 206 | Memory |
| 208 | Capturing device |
| 300 | Data |
| 302 | Image Information |
| 304 | Region of Interest Data |
| 306 | Video Plethysmographic Waveforms Data |
| 308 | $SPO_2$ |
| 310 | Environmental oxygen level data |
| 312 | Predefined oxygen level data |
| 314 | Other Data |
| 316 | Modules |
| 318 | Receiving Module |
| 320 | ROI Detection Module |
| 322 | Video Plethysmographic Waveform Generation Module |
| 324 | Oxygen Estimation Module |
| 326 | Comparison Module |
| 328 | Output Module |
| 330 | Other Module |
| 600 | Computer System |
| 601 | I/O Interface |
| 602 | Processor |
| 603 | Network Interface |
| 604 | Storage Interface |
| 605 | Memory |
| 606 | User Interface |
| 607 | Operating System |
| 608 | Web Server |
| 609 | Communication Network |
| 610a, . . . , 610n | User Devices |
| 611a, . . . , 611n | Servers |
| 612 | Input Devices |
| 613 | Output Devices |
| 614 | Capturing device |

We claim:

1. A method for improving oxygen supply to an environment, the method comprising:

receiving, by a monitoring device, a number of video frames containing at least one image of an environment comprising a plurality of users, from a capturing device;

detecting, by the monitoring device, at least one region of interest of each of the plurality of users in the at least one image;

generating, by the monitoring device, a color histogram using pixel data of the at least one region of interest for each of the plurality of users, each color histogram comprising a plurality of different color channels;

generating, by the monitoring device, a video plethysmographic waveform for each color channel of the color histograms;

determining, by the monitoring device and from pixel value variations in each of the video plethysmographic waveforms, a first value representing a level of hemoglobin of blood for each of the plurality of users and a second value representing a level of oxy-hemoglobin of blood for each of the plurality of users, for each of the number of video frames;

determining, by the monitoring device, peripheral capillary oxygen saturation ($SPO_2$) level of each of the plurality of users by computing a ratio between the first value and the second value averaged across the number of video frames;

determining, by the monitoring device and from an average of the $SPO_2$ levels determined for each of the plurality of users, an oxygen level of the environment;

comparing, by the monitoring device, the oxygen level of the environment with a predefined oxygen level for the environment; and increasing, by the monitoring device, oxygen supply to the environment determined from a result of the comparison, wherein the monitoring device is a non-invasive device.

2. The method as claimed in claim 1, wherein the region of interest comprises uncovered body parts of the user.

3. The method as claimed in claim 1, wherein the at least one image is divided into plurality of clusters, wherein each cluster of the plurality of clusters comprises a predefined number of users of the plurality of users.

4. The method as claimed in claim 3, further comprising averaging $SPO_2$ of the predefined number of users to determine first average of $SPO_2$ of each the plurality of clusters.

5. The method as claimed in claim 4 further comprising averaging the first average of $SPO_2$ of each of the plurality of clusters to obtain an average $SPO_2$.

6. The method as claimed in claim 1, wherein the one or more actions is at least one of, monitoring the oxygen level, storing the oxygen level for further analysis, providing a notification to a display unit and providing supply of oxygen to the environment.

7. A monitoring device for improving oxygen supply to an environment, the monitoring device comprising:
a processor; and
a memory communicatively coupled to the processor, wherein the memory stores processor-executable instructions, which, on execution, causes the processor to:
receive a number of video frames containing at least one image of an environment comprising plurality of users, from a capturing device;
detect at least one region of interest of each of the plurality of users in the at least one image;
generate a color histogram using pixel data of the at least one region of interest for each of the plurality of users, each color histogram comprising a plurality of different color channels;

generate a video plethysmographic waveform for each color channel of the color histograms;

determine, from pixel value variations in each of the video plethysmographic waveforms, a first value representing a level of hemoglobin of blood for each of the plurality of users and a second value representing a level of oxy-hemoglobin of blood for each of the plurality of users, for each of the number of video frames;

determine, peripheral capillary oxygen saturation ($SPO_2$) level of each of the plurality of users by computing a ratio between the first value and the second value averaged across the number of video frames;

determine, from an average of the $SPO_2$ levels determined for each of the plurality of users, an oxygen level of the environment;

compare the oxygen level of the environment with a predefined oxygen level for the environment; and increase oxygen supply to the environment determined from a result of the comparison, wherein the monitoring device is a non-invasive device.

8. The monitoring device as claimed in claim 7, wherein the region of interest comprises uncovered body parts of the user.

9. The monitoring device as claimed in claim 7, wherein the at least one image is divided into plurality of clusters, wherein each cluster of the plurality of clusters comprises a predefined number of users of the plurality of users.

10. The monitoring device as claimed in claim 9, wherein the processor is further configured to average $SPO_2$ of the predefined number of users to determine first average of $SPO_2$ of each the plurality of clusters.

11. The monitoring device as claimed in claim 10, wherein the processor is further configured to average the first average of $SPO_2$ of each of the plurality of clusters to obtain an average $SPO_2$.

12. The monitoring device as claimed in claim 7, wherein the one or more actions is at least one of, monitoring the oxygen level, storing the oxygen level for further analysis, providing a notification to a display unit and providing supply of oxygen to the environment.

13. A non-transitory computer readable medium including instructions stored thereon that when processed by at least one processor cause a device to perform operations comprising:
receiving, a number of video frames containing at least one image of an environment comprising plurality of users, from a capturing device;
detecting at least one region of interest of each of the plurality of users in the at least one image;
generating a color histogram using pixel data of the at least one region of interest for each of the plurality of users, each color histogram comprising a plurality of different color channels;
generating a video plethysmographic waveform for each color channel of the color histograms;
determining, from pixel value variations in each of the video plethysmographic waveforms, a first value representing a level of hemoglobin of blood for each of the plurality of users and a second value representing a level of oxy-hemoglobin of blood for each of the plurality of users, for each of the number of video frames;

determining peripheral capillary oxygen saturation (SPO$_2$) level of each of the plurality of users by computing a ratio between the first value and the second value averaged across the number of video frames;

determining, from an average of the SPO$_2$ levels determined for each of the plurality of users, an oxygen level of the environment;

comparing the oxygen level of the environment with a predefined oxygen level for the environment; and increasing oxygen supply to the environment determined from a result of the comparison, wherein the oxygen supply is increased to the environment non-invasively.

14. The medium as claimed in claim 13, wherein the region of interest comprises uncovered body parts of the users of the plurality of users.

15. The medium as claimed in claim 13, wherein the at least one image is divided into plurality of clusters by the processor, wherein each cluster of the plurality of clusters comprises predefined number of users.

16. The medium as claimed in claim 13, wherein the instructions further causes the processor to average SPO$_2$ of the predefined number of users to determine first average of SPO$_2$ of each the plurality of clusters.

* * * * *